(12) United States Patent
López-Bucio et al.

(10) Patent No.: US 8,536,091 B2
(45) Date of Patent: Sep. 17, 2013

(54) SYSTEM FOR PROTECTION OF PLANTS FROM PATHOGENS USING ALKAMIDES

(76) Inventors: José López-Bucio, Morelia (MX); Jorge Molina-Torres, Irapuato (MX); Luis Rafael Herrera-Estrella, Irapuato (MX)

( * ) Notice: Subject to any disclaimer, the term of this patent is extended or adjusted under 35 U.S.C. 154(b) by 10 days.

(21) Appl. No.: 13/057,993

(22) PCT Filed: Aug. 5, 2009

(86) PCT No.: PCT/IB2009/006677
§ 371 (c)(1),
(2), (4) Date: Feb. 7, 2011

(87) PCT Pub. No.: WO2010/015932
PCT Pub. Date: Feb. 11, 2010

(65) Prior Publication Data
US 2011/0136668 A1    Jun. 9, 2011

Related U.S. Application Data

(60) Provisional application No. 61/188,058, filed on Aug. 5, 2008.

(51) Int. Cl.
*A01N 37/18*    (2006.01)
*A01N 25/26*    (2006.01)
*A01P 3/00*    (2006.01)

(52) U.S. Cl.
USPC ............ 504/100; 504/101; 504/339; 514/625

(58) Field of Classification Search
USPC .......................... 504/339, 100, 101; 514/625
See application file for complete search history.

(56) References Cited

U.S. PATENT DOCUMENTS 6,841,572 B2    1/2005    Horst et al.
7,141,686 B2    11/2006    Dewis et al.

OTHER PUBLICATIONS

Molina-Torres et al. "Fungistatic and Bacteriostatic Activities of Alkamides from *Heliopsis longipes* Roots: Affinin and Reduced Amides." J. Agric. Food Chem. 2004, 52:4700-4704.
Ramirez-Chavez et al. "Alkamides Isolated from Plants Promote Growth and Alter Root Development in *Arabidopsis*." Plant Physiology, 2004, 134:1058-1068.
Young, Lee W., Authorized officer, International Searching Authority, International Search Report, PCT Patent Application Serial No. PCT/IB09/06677; search completion date: Jan. 8, 2010; search mailing date: Feb. 3, 2010.
Young, Lee W., Authorized officer, International Searching Authority, Written Opinion of the International Searching Authority, PCT Patent Application Serial No. PCT/IB09/06677; search completion date: Jan. 8, 2010; search mailing date: Feb. 3, 2010.

*Primary Examiner* — John Pak
*Assistant Examiner* — Andriae M Holt
(74) *Attorney, Agent, or Firm* — Kolisch Hartwell, P.C.

(57) ABSTRACT

System, including methods compositions, and kits, for controlling the growth of fungi and other pathogens in plants using at least one alkamide, which may function by increasing or eliciting natural defense mechanisms of the plants against such pathogens.

13 Claims, No Drawings

SYSTEM FOR PROTECTION OF PLANTS FROM PATHOGENS USING ALKAMIDES

CROSS-REFERENCE TO PRIORITY APPLICATION

This application is based upon and claims the benefit under 35 U.S.C. §119(e), the Paris Convention priority right, and any and all other applicable law, of U.S. Provisional Patent Application Ser. No. 61/188,058, filed Aug. 5, 2008, which is incorporated herein by reference in its entirety for all purposes.

BACKGROUND

Agricultural production is under constant stress from global population growth. Climate change, loss of arable land, and pathogenic parasites (insects and microorganisms) continually threaten agricultural production. New technologies, such as creation of transgenic plants and genetic inbreeding, have helped increase agricultural output, but are by no means a general solution. The high cost of fuel, fertilizers, and pesticides have also considerably increased the cost of food and endanger a constant food supply for the developing world.

Plants continuously respond to abiotic and biotic stress by adjusting their metabolism and activating diverse intracellular signaling responses. In particular, modifications of plant architecture in response to physical or chemical stimuli or the activation of pathogen-specific defense mechanisms upon microbial infection permits plant survival and reproduction. Classic signaling molecules, such as auxin, cytokinin, gibberellins, abscisic acid (ABA), and brassinosteroids, have been extensively studied in the context of their role in morphogenetic processes, whereas jasmonic acid (JA), ethylene, and salicylic acid (SA) have been found to participate in defense-responses against pathogens.

A novel group of lipid-derived plant metabolites, known as alkamides, has been shown recently to alter plant metabolism and development. Alkamides comprise over 200 related compounds that have been found in as many as 10 plant families: Aristolochiaceae, Asteraceae, Brassicaceae, Convolvulaceae, Euphorbiaceae, Menispermaceae, Piperaceae, Poaceae, Rutaceae, and Solanaceae. Plant-produced alkamides have been found to alter root and shoot system architecture in Arabidopsis by affecting cell division and differentiation processes. Morphogenetic responses affected by alkamides included primary root growth, lateral and adventitious root formation, root hair formation, and leaf development.

Alkamides have also been reported to have in vitro antimicrobial activity, in the absence of plants. For example, affinin has been demonstrated to inhibit the growth of some microbial plant pathogens, including bacteria and fungi. However, a reduced form of affinin, N-isobutyl decanamide, has been reported to lack a fungistatic activity that is present in affinin. In any event, relatively high levels of alkamides have been utilized to demonstrate in vitro antimicrobial activity, potentially making alkamides too expensive for large-scale use as antimicrobials.

Plants posses various inducible defense mechanisms to protect themselves against pathogen attack. For example, systemic acquired resistance (SAR) is activated in plants after infection by necrotizing pathogens. Similarly, colonization of plant roots by certain non-pathogenic rhizobacteria can elicit induced systemic resistance (ISR) in the host plant. ISR is a plant-mediated mechanism initiated at the root that extends up to the shoot. Similar to SAR, ISR is effective against different types of plant pathogens.

With the high cost and scarcity of food, increasing agricultural production and efficiency is key worldwide. Control of pathogens, especially bacteria and fungi, is important to enable increased production of food and better use of fertile land, but there is a growing awareness of the potential toxicity of standard pesticides. Thus, organically grown produce and grains are becoming important and growing markets. The use of natural, low cost pesticides, such as pesticides that induce natural defense mechanisms of plants, may significantly improve the outlook of the food supply worldwide and may, at the same time, provide eco-friendly pest control systems.

SUMMARY

The present disclosure provides a system, including methods, compositions, and kits, for controlling the growth of fungi and other pathogens in plants using at least one alkamide, which may function by increasing or eliciting natural defense mechanisms of the plants against such pathogens.

DETAILED DESCRIPTION

The present disclosure provides a system, including methods, compositions, and kits, for controlling the growth of fungi and other pathogens in plants using at least one alkamide, which may function by increasing or eliciting natural defense mechanisms of the plants against such pathogens.

Alkamides are a family of natural occurring compounds, which upon isolation, or chemical synthesis, and subsequent application, may strongly stimulate natural resistance in plants against pathogenic fungi and bacteria (and other pathogens and parasites). Thus, alkamides may become a new type of powerful, eco-friendly pesticide for a wide variety of plants. This family of compounds could act as powerful "defense elicitors" in plants and could have great potential application in combating pathogenic pests. Alkamides, such as N-isobutyl decanamide, can be key in triggering adjustment of anatomical characteristics by the plant under attack, enabling it to mount a better defense response, and additionally, limiting its exposure to unfavorable environmental conditions.

The present disclosure presents data involving treatment of *Arabidopsis* (*A. thaliana*) with N-isobutyl decanamide. The data show that N-isobutyl decanamide induces many defense-related genes, in addition to inducing genes potentially involved in growth and development. The increased expression of defense response genes occurs in parallel with accumulation of free and glucoside-conjugated salicylic acid in seedlings. N-isobutyl decanamide was found, when tested on Arabidopsis seedlings, to be the most active alkamide identified to date. The data also show that application of this compound to a plant confers resistance against fungal necrotizing pathogens. When tested against the necrotizing fungi *Botrytis cinerea* and *Alternaria brassicicola*, N-isobutyl decanamide significantly reduced necrosis caused by the pathogens and inhibited fungal proliferation on leaves when compared to the controls. The data further show that N-isobutyl decanamide can modulate salicylic acid-associated defense responses, which lead to increased resistance against fungal pathogens. Thus, alkamides like N-isobutyl decanamide represent a new, biologically and ecologically friendly, system of control of pathogenic fungi and other pathogens in plants using powerful, eco-friendly pesticides.

The present disclosure provides a method of plant protection using at least one member of a family of compounds, alkamides, as natural pest controlling agents. These compounds may trigger or stimulate high resistance in plants against pathogens. Alkamides belong to a class of bioactive, amino lipids of wide distribution in plants. The method may involve selecting a suitable plant and applying an effective amount of an alkamide to the plant, as described below.

At least one plant may be selected. The plant may be any type of plant, at any stage of plant development (e.g., a seed, seedling, mature plant, etc.). The plant also may be a isolated portion of a plant, for example, in connection with plant propagation (e.g., a bud, bulb, callus, corm, cutting, plantlet, rhizome, rootstock, scion, stolon, tissue culture, tuber, etc.). The plant may be susceptible to infection by a pathogen or may already be infected by the pathogen. Exemplary pathogens that the plant may be susceptible to and/or infected by include viruses, bacteria, protozoans, fungi, and the like.

A composition comprising an alkamide may be applied to the selected plant(s). The alkamide may have the following general formula:

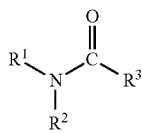

$R^1$ and $R^2$ each, independently, may be hydrogen or an organic moiety having 1 to 8 carbons, 1 to 6 carbons, or 4 carbons, among others. In some embodiments, $R^1$ may be isobutyl and $R^2$ may be hydrogen. $R^3$ may be an organic moiety having 8 to 13 carbons, or 9 to 11 carbons (e.g., 9, 10, or 11 carbons), optionally unsaturated at one, two, three, or more positions. The carbonyl shown above is at position number 1, with the adjacent, first carbon of $R^3$ being at position number 2. If unsaturated, $R^3$ may be unsaturated at any one position or combination of positions 2-10, such as one or more of positions 2, 4, 6, or 8, among others, with each unsaturation being of the E or Z form. In some embodiments, the alkamide may be affinin, which is N-isobutyl-deca-2E, 6Z,8E-trieneamide. In some embodiments, $R^3$ has 9 carbons, and is unsaturated at position 2 only, such as in the E form. For example, the alkamide may be N-isobutyl-2E-decenamide. In some embodiments, the alkamide may be N-isobutyl decanamide:

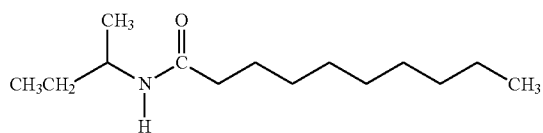

The amount of alkamide applied to the selected plant(s) may be an effective amount, that is, an amount sufficient to inhibit pathogen growth, attack, and/or infection by inducing a defense response to pathogens in the plant. A "defense response," as used herein, is a response involving changes in gene expression in the plant and resulting in an increased expression of one or more defense-related plant genes (e.g., PR1) and/or increased levels of one or more defense-related plant compounds, such as free/conjugated salicylic acid and/or free/conjugated jasmonic acid. An exemplary effective amount may be provided by an alkamide disposed in a composition at a concentration of less than about $10^{-6}$ M, $10^{-7}$ M, $10^{-8}$ M, or $10^{-9}$ M, such as about $10^{-6}$ to $10^{-12}$ M, or $10^{-8}$ to $10^{-12}$ M, among others. The composition may be aqueous and/or may include one or more salts, buffers, surfactants (ionic or nonionic), plant nutrients/fertilizers, or plant hormones (one of or any combination of an auxin, a cytokinin, a gibberellin, abscisic acid (ABA), a brassinosteroid, jasmonic acid (JA), ethylene, and salicylic acid (SA)), or any combination thereof.

The alkamide may be applied to the plant selected by any suitable mechanism(s). The alkamide may be applied as a liquid or solid formulation, among others. For example, the alkamide may be sprayed onto the plant (such as in an aerosol or surface spray, among others), applied to a growth medium (e.g., soil) in which plant is disposed, spread on a portion of the plant, or the like. Alternatively, or in addition, a portion or all of the plant may be dipped in an alkamide composition. In an event, application of the alkamide may include contacting (a) a composition including an alkamide and (b) one or more leaves, shoots, or roots of the plant. The application may include a seed treatment; foliar spray; soil drench; pseudostem, root, stem, or trunk injection; fruit or root dip; row treatment; etc.

The alkamide may be obtained from any suitable source(s) by any suitable procedure or set of procedures. For example, the alkamide, or an oxidized precursor of the alkamide, may be obtained from a natural source, such as one or more plants. In some embodiments, the alkamide or precursor may be isolated by solvent extraction, supercritical fluid extraction, or a combination thereof. Alternatively, or in addition, the alkamide or precursor may be provided through organic synthesis, which optionally may be catalyzed by one or more enzymes. In some cases, the alkamide may be produced via chemical reduction, outside plants, of an oxidized precursor, which, in turn, may have been isolated from plants. Chemical reduction may, for example, be performed with hydrogen gas, a catalyst (e.g., platinum), an enzyme, or a combination thereof, among others.

EXAMPLE 1

N-isobutyl Decanamide Affects Growth and Development of *Arabidopsis* Seedlings Without Compromising Cell Viability One of the effects of alkamides on plants is the dose-dependent inhibition of primary root growth. Experiments were performed to validate the biological activity of N-isobutyl decanamide on *Arabidopsis* seedlings prior to characterization of global gene expression responses, and to explore whether this inhibition of primary root growth could be due to a developmental rather than to possible cytotoxic effects. *Arabidopsis* seedlings were germinated for 6 d on agar plates containing 0.2× Murashige and Skoog (MS) medium, and then transferred to plates containing MS 0.2× agar medium supplied with 60 pM N-isobutyl decanamide or solvent alone (as control). Seven days after transfer (d.a.t.), plants exposed to the solvent continued their normal growth, producing normal leaves and a typical root system with proliferating lateral roots. In contrast, N-isobutyl decanamide-treated seedlings showed inhibition of shoot and root growth, greening of leaves, formation of increased numbers of adventitious and lateral roots, and formation of callus-like structures on leaf blades.

It was also determined that primary root growth inhibition was not due to a toxic effect but rather to an effect of N-isobutyl decanamide on cell division or elongation.

These results suggest that the effects of N-isobutyl decanamide on root development involve changes in cellular processes without affecting cell viability or integrity.

EXAMPLE 2

Transcription Profiling of N-isobutyl Decanamide Effects

Transcription profiling of the effect of alkamides on *Arabidopsis* seedlings was performed. N-isobutyl decanamide was found to be the most active alkamide identified to date. A global analysis of gene expression changes in response to N-isobutyl decanamide treatment in *Arabidopsis thaliana* revealed 1,017 differentially regulated genes (579 were up-regulated and 437 genes were down-regulated). When up-regulated genes were categorized by function, it was observed that several gene families involved in plant growth and development, and many others in plant defense responses, were also up-regulated (including chitinases and plant defensins and others).

EXAMPLE 3

N-isobutyl Decanamide Induces Accumulation of Compounds Involved in Defense Mechanisms The levels of two important compounds involved in mediating defense mechanisms in plants, salicylic acid (SA) and jasmonic acid, were quantified after treatment with N-isobutyl decanamide. A three- to four-fold increase in the relative levels of free SA, as well as conjugated SA, was observed in N-isobutyl decanamide-treated plants when compared to controls. This experiment shows that N-isobutyl decanamide may stimulate defense responses through these two compounds.

EXAMPLE 4

N-isobutyl Decanamide Induces the Expression of PR1

Salicylic acid is known to induce plant resistance to a number of pathogenic microbes in a process known as systemic acquired resistance (SAR). The PR1 (pathogenesis-related 1) gene has been implicated at least in part in the induction of disease resistance in plants. Our gene expression analysis revealed a 2.5-, 4.3-, and 7.2-fold induction in PR1 (At2g14610) mRNA expression at 1 d, 3 d, and 7 d, respectively, after transfer of seedlings to N-isobutyl decanamide-containing medium, suggesting an early response of the PR1 gene (a plant defense marker) to this alkamide.

Tests were performed to determine whether PR1 expression is activated by N-isobutyl decanamide at the transcriptional level. Transgenic A. thaliana seedlings containing a chimeric gene in which the PR1 promoter is fused to the GUS reporter gene (PR1:GUS) were treated with 60 pM N-isobutyl decanamide. GUS histochemical determinations then were performed in 10 d-old seedlings. Control seedlings did not show PR1:GUS expression in roots or shoots. Interestingly, PR1:GUS expression was observed in sections of shoots and roots in alkamide-treated seedlings. When detached leaves from adult Arabidopsis plants were exposed to N-isobutyl decanamide for 3 d, a uniform and high level of PR1:GUS was detected in control leaves.

EXAMPLE 5

N-isobutyl Decanamide Confers Resistance to Fungal Necrotrophic Pathogens *Botrytis cinerea* and *Alternaria brassicicola*

Our results from microarray experiments showing SA accumulation and PR1 induction suggest that N-isobutyl decanamide may be detected by plants as a potential defense inducing factor similar to those produced by avirulent pathogens leading to plant resistance. To study whether N-isobutyl decanamide could effectively activate defense mechanisms, we tested the response, of leaves from 20 d-old *Arabidopsis* plants, to necrotrophic pathogens *Alternaria brassicicola* and *Botrytis cinerea*. These pathogens provoke spreading necrotic lesions on leaves. In these experiments, fully developed leaves from 20 day-old plants were transferred to medium supplied with N-isobutyl decanamide or with the solvent as control. *A. brassicicola* and *B. cinerea* spores were inoculated on the leaf surface and disease symptoms evaluated 3 d, 4 d, and 5 d after inoculation (d.a.i.). In leaves transferred to control medium and inoculated for 3 d, the two pathogens were found to induce necrotic lesions in over 90% of inoculated leaves. On the other hand, in leaves treated with N-isobutyl decanamide for 3 d, about 30% of leaves presented necrotic lesions caused by *A. brassicicola* and only about 10% by *B. cinerea* attack.

It was also observed that lesions on untreated leaves were about 6 mm in diameter, while lesions on leaves treated with N-isobutyl decanamide were of a much smaller diameter, about 0.8-1.5 mm. Visual inspection showed that control leaves inoculated with the pathogens had generalized necrotic lesions spanning half or more the surface of the leaf at 4 d.a.i., while the alkamide-treated leaves presented milder symptoms.

Next, growth of the pathogens was monitored by direct microscopic observation of stained hyphae in infected leaves. It was found that disease symptoms in control leaves at day 3 after inoculation with *A. brassicicola* were accompanied by prolific growth of fungal hyphae, which correlated with increased damage of leaf tissue. However, N-isobutyl decanamide treatment inhibited fungal development, resulting in decreased degradation of leaf tissue. A similar protective effect of the alkamide could be observed in leaves inoculated with *B. cinerea*, where a decrease in fungal growth and disease symptoms on leaves was observed. On the basis of all these findings, it can be concluded that N-isobutyl decanamide treatment engenders enhanced resistance to necrotizing fungi.

EXAMPLE 6

Selected Embodiments

This example describes selected embodiments of the present disclosure, presented as a series of indexed paragraphs. In particular, this example describes methods of using alkamides to protect plants from pathogens.

1. A method for using at least one member of a family of compounds called alkamides as a defense elicitor or natural pesticide to protect plants against the attack of pathogenic microorganisms.

2. A method for using at least one member of a family of compounds called alkamides as a defense elicitor or natural pesticide to protect plants against the attack of pathogenic fungi, bacteria, parasites, viruses, and common plant pests.

3. The method described in paragraph 2 or 3, where the alkamide is N-isobutyl decanamide.

4. The method of any of paragraphs 1-3, where one alkamide or a combination of two or more alkamides is used as a defense elicitor or natural pesticide, to protect plants against the attack of pathogenic fungi, bacteria, and/or viruses.

5. The method of any of paragraphs 1-3, where one alkamide or a combination of two or more alkamides is used as a defense elicitor or natural pesticide, to protect plants against the attack of pathogenic fungi.

6. The method of any of paragraphs 1-3, where one alkamide or a combination of two or more alkamides is used as a defense elicitor or natural pesticide to protect plants against the attack of necrotrophic plant fungi.

7. The method any of paragraphs 1-3, where one alkamide or a combination of two or more alkamides is used as a defense elicitor or natural pesticide to protect plants against the attack of the pathogenic plant fungi *Alternaria* sp., *Botrytis* sp., or both.

8. The method of paragraph 1, where the alkamide(s) is extracted from at least one natural source by traditional solvent extraction, supercritical solvent extraction (SFE), by organic synthesis, or with the use of enzymes in organic solvents.

9. The method of paragraph 1, where the alkamide(s) is produced synthetically or partially synthetically from precursors.

10. The method of paragraph 1 where the alkamide(s) is used in conjunction with other pathogen controlling agents or defense elicitors to protect plants against the attack of pathogenic microorganisms or other pests or parasites.

11. The method of paragraph 1, where the alkamide(s) is applied through one or several routes of application, such as aerosol, direct application on plants or seedlings, and/or combined with other nutrients or combined with fertilizers.

12. The method of paragraph 1, where the alkamide(s) is provided in a kit for its subsequent application in plants.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of plant protection, comprising: selecting a plant susceptible to infection by a fungus, wherein the fungus is selected from the group consisting of the genera Alternaria and Botrytis; and
applying an effective amount of N-isobutyl decanamide to the plant to inhibit growth of the fungus.

2. The method of claim 1, wherein the N-isobutyl decanamide is extracted from a natural source.

3. The method of claim 2, wherein the N-isobutyl decanamide is extracted from the natural source by traditional solvent extraction or supercritical fluid extraction (SFE).

4. The method of claim 1, wherein the N-isobutyl decanamide is produced synthetically from a precursor.

5. The method of claim 4, wherein the precursor is affinin.

6. The method of claim 1, wherein the step of applying includes a step of applying the effective amount as an aerosol, as a liquid fertilizer composition, by dipping at least a portion of the plant into a composition containing the N-isobutyl decanamide, or any combination thereof.

7. The method of claim 1, wherein the plant is a seed and/or seedling when application of N-isobutyl decanamide starts.

8. The method of claim 1, further comprising a step of applying at least one other pathogen-controlling agent or defense elicitor to protect the plant against attack by a pathogenic microorganism, pest, and/or parasite.

9. The method of claim 1, further comprising a step of obtaining a kit including a composition comprising the N-isobutyl decanamide and configured for application to plants.

10. The method of claim 1, wherein the step of selecting selects a plant already infected with the fungus.

11. The method of claim 1, wherein the step of applying includes a step of contacting (a) a composition including N-isobutyl decanamide to (b) one or more leaves, shoots, or roots of the plant, or any combination thereof.

12. The method of claim 1, wherein the step of applying includes a step of applying the N-isobutyl decanamide in a liquid or solid formulation.

13. The method of claim 1, wherein the step of applying includes a step of applying an amount of N-isobutyl decanamide sufficient to kill the fungus.

* * * * *